(12) United States Patent
Housley et al.

(10) Patent No.: US 7,060,853 B2
(45) Date of Patent: *Jun. 13, 2006

(54) METHOD FOR INCREASING OXIDATION REACTOR PRODUCTION CAPACITY

(75) Inventors: Samuel Duncan Housley, Yarm (GB); John A. Turner, Stokesley (GB)

(73) Assignee: Invista North America S.a r.l., Wilmington, DE (US)

( * ) Notice: Subject to any disclaimer, the term of this patent is extended or adjusted under 35 U.S.C. 154(b) by 198 days.

This patent is subject to a terminal disclaimer.

(21) Appl. No.: 10/394,298

(22) Filed: Mar. 21, 2003

(65) Prior Publication Data

US 2003/0229248 A1    Dec. 11, 2003

Related U.S. Application Data

(63) Continuation-in-part of application No. 09/884,184, filed on Jun. 19, 2001, now abandoned, which is a continuation-in-part of application No. 09/757,455, filed on Jan. 10, 2001, now abandoned, which is a continuation-in-part of application No. 09/481,811, filed on Jan. 12, 2000, now abandoned.

(51) Int. Cl.
    *C07C 51/16* (2006.01)

(52) U.S. Cl. .................. 562/412; 562/414; 562/413; 562/416; 562/77

(58) Field of Classification Search ............... 562/414, 562/413, 412, 77, 416
See application file for complete search history.

(56) References Cited

U.S. PATENT DOCUMENTS

| 3,686,293 A | 8/1972 | Gualdi et al. |
| 4,269,805 A | 5/1981 | Schoengen et al. |
| 4,593,122 A | 6/1986 | Hashizume et al. |
| 5,004,830 A | 4/1991 | Park et al. |

FOREIGN PATENT DOCUMENTS

| WO | WO 99/31038 | 6/1999 |
| WO | WO 99/59953 | 11/1999 |

*Primary Examiner*—Cecilia J. Tsang
*Assistant Examiner*—Taylor Victor Oh
(74) *Attorney, Agent, or Firm*—Charles E. Krukiel

(57) ABSTRACT

The present invention relates to a method for increasing the production capacity of a conventional oxidation reactor for catalytic liquid phase oxidation of paraxylene by staging the oxidation reaction into a first high pressure and high solvent ratio reaction zone followed by the conventional reactor.

16 Claims, 2 Drawing Sheets

METHOD FOR INCREASING OXIDATION REACTOR PRODUCTION CAPACITY

CROSS REFERENCE TO RELATED APPLICATION

This application claims priority benefit of U.S. patent application Ser. No. 09/884,184 filed 19 Jun. 2001, pending, U.S. patent application Ser. No. 09/481,811 filed 12 Jan. 2000, U.S. patent application Ser. No. 09/757,455 filed 10 Jan. 2001 and U.S. application Ser. No. 09/757,458 filed 10 Jan. 2001, all abandoned.

BACKGROUND OF THE INVENTION

The present invention relates to a method for increasing the rated capacity of a commercial oxidation reactor. More particularly, the present invention is a method for debottlenecking a commercial reactor system of the type used for catalytic liquid phase oxidation of paraxylene to produce terephthalic acid.

Practically all terephthalic acid is produced on a commercial scale by catalytic, liquid phase, air oxidation of paraxylene. Commercial processes use acetic acid as a solvent and a multivalent heavy metal or metals as catalyst. Cobalt and manganese are the most widely used heavy metal catalysts, and bromine is used as a renewable source of free radicals in the process.

In conventional air-oxidation processes, acetic acid solvent, air (molecular oxygen), paraxylene and catalyst are fed continuously into a back-mixed oxidation reactor that is maintained at from 150° C. to 225° C. and from about 500 to 2,500 kPa (i.e., 5–25 atm). In such conventional oxidation reactors, the feed solvent:paraxylene mass ratio is typically less than 5:1. Air is added to the reactor in amounts in excess of the stoichiometric requirements for full conversion of the paraxylene to terephthalic acid to minimize formation of undesirable by-products, such as color formers. The oxidation reaction is exothermic, and heat is removed from the reactor by allowing the acetic acid solvent to vaporize. The corresponding vapor is condensed and most of the condensate is refluxed to the reactor, with some condensate being withdrawn to control water concentration in the system (two moles of water are formed per mole of paraxylene reacted to terephthalic acid). The reactor residence time is typically 30 minutes to 2 hours, depending on the process. Depending on oxidation reactor operating conditions, e.g., temperature, catalyst concentration and residence time, significant degradation of the solvent and precursor can occur, which, in turn, can increase the cost of operating the process. Such conventional oxidation reactors are well known, for example, see U.S. Pat. No. 5,099,064.

The effluent, i.e., reaction product, from the oxidation reactor is a slurry of crude terephthalic acid (TA) crystals in acetic acid. A significant and undesirable impurity in the crude TA is 4-carboxybenzaldehyde (4-CBA), which is incompletely oxidized paraxylene, although p-tolualdehyde and p-toluic acid can also be present along with undesirable color formers. The slurry of crude terephthalic acid crystals is further processed (e.g., purified by post-oxidation and/or hydrogenation) and recovered (e.g., by filtration, washing and drying) according to established methods.

The present invention provides a reliable and affordable method to increase the production capacity of a conventional terephthalic acid process by up to 100% by increasing the capacity of the oxidation reactor system, i.e., "debottlenecking" the reactor system. Debottlenecking is achieved according to the invention by effectively staging the oxidation reaction utilizing a first reaction zone, i.e., first reactor, followed by a second reaction zone, i.e., the existing, conventional reactor.

SUMMARY OF THE INVENTION

The present invention is a method for increasing the production capacity of a conventional back-mixed oxidation reactor for producing aromatic carboxylic acids by catalytic liquid phase oxidation of a corresponding precursor in a suitable solvent. In particular, the present invention is a method for increasing the production capacity of an existing conventional back-mixed oxidation reactor for the catalytic liquid phase oxidation of paraxylene.

According to the invention, a first reaction zone, or first reactor, is positioned upstream of the existing conventional oxidation reactor, and the method is accomplished according to the sequential steps of feeding the reactants, including a suitable solvent, which is acetic acid, to the first reaction zone at elevated pressure wherein the solvent ratio (i.e., the acetic acid:paraxylene mass ratio) and the uptake of oxygen are controlled such that any terephthalic acid which forms in the first reaction zone remains in solution, and then feeding the resulting reaction medium to the conventional, i.e., second, oxidation reaction zone.

In a preferred embodiment of the invention, the method comprises:

(a) feeding acetic acid, oxidation catalyst, paraxylene, and a supply of oxygen to a first reaction zone to form a reaction medium in which the acetic acid:paraxylene mass ratio is in the range of from 5–30:1 and the operating pressure is at least about 2,500 kPa;

(b) limiting the uptake of oxygen within the reaction medium in said first reaction zone to a value which is less than that required for full conversion of the paraxylene to terephthalic acid such that any terephthalic acid which forms substantially remains in solution; and (c) feeding the reaction medium to a second reaction zone, which is the existing conventional back-mixed oxidation reactor, while simultaneously reducing the pressure of the reaction medium to a value in the range of from about 500 kPa to less than 2,500 kPa.

Terephthalic acid resulting from the second reaction zone, which is typically a slurry of terephthalic acid crystals, can be further processed and recovered according to any convenient method.

The preferred acetic acid:paraxylene mass ratio for economy and process operability is from 13–16:1.

One aspect of the invention is that the terephthalic acid (TA) formed in the first reaction zone remains substantially in solution. By "substantially," the inventors mean that it is preferred to have very little, e.g., less than about 10 percent by weight of solid TA precipitate from solution in the first reaction zone. It is more preferred to have only a trace, e.g., less than 1 percent of solid TA precipitate from solution in the first reaction zone. It is most preferred to avoid precipitation of solid terephthalic acid in the first reaction zone.

Formation of terephthalic acid in the first reaction zone is limited by limiting oxygen uptake in the first reaction zone. Precipitation of terephthalic acid is prevented within the first reaction zone by maintaining a high acetic acid:paraxylene mass ratio, by maintaining a sufficiently high reaction medium temperature, and by selecting an appropriate coolant (e.g., boiling water) and cooling means that avoids cold spots from forming at any location within the reaction zone.

The uptake of oxygen in the first reaction zone is limited to a value below that required for full conversion of the paraxylene present to terephthalic acid to prevent significant quantities of TA being formed and solids being precipitated. Preferably, the oxygen uptake within the reaction medium in the first reaction zone is less than 70 percent of the oxygen required for full conversion of the paraxylene present to terephthalic acid. More preferably, the oxygen uptake will lie in the range of from 40–60% of the oxygen required for full conversion of the paraxylene present.

Oxygen uptake in the first reaction zone is controlled by one or more of the following methods: (i) maintaining oxygen supply within a predetermined range, (ii) maintaining catalyst concentration within a predetermined range, (iii) limiting the residence time (defined as the reactor liquid volume divided by the reactor feed rate) within the first reaction zone to less than about 6 minutes, but preferably less than 4 minutes, and (iv) optionally removing heat from, i.e., cooling, the reaction medium. According to a preferred embodiment of the invention, oxygen is dissolved directly into a feed stream comprising acetic acid and oxidation catalyst, and the oxygenated feed stream is then fed continuously and simultaneously with paraxylene into the first oxidation reaction zone, which is a plug flow reaction zone. Immediately upon entering the first reaction zone the paraxylene is thoroughly mixed with the oxygenated acetic acid to thereby initiate the reaction. By controlling the oxygen supply, catalyst concentration, residence time and optionally the temperature of the first reaction zone, it is possible to control, i.e., limit, the uptake of oxygen within the first reaction zone to a value which is less than that required for full conversion of the paraxylene present to terephthalic acid such that any terephthalic acid which forms substantially remains in solution. The reaction medium from the first reaction zone is then fed to the second reaction zone, which is the existing, conventional back-mixed oxidation reactor.

BRIEF DESCRIPTION OF THE DRAWING(S)

DETAILED DESCRIPTION OF THE INVENTION

Figure 1:
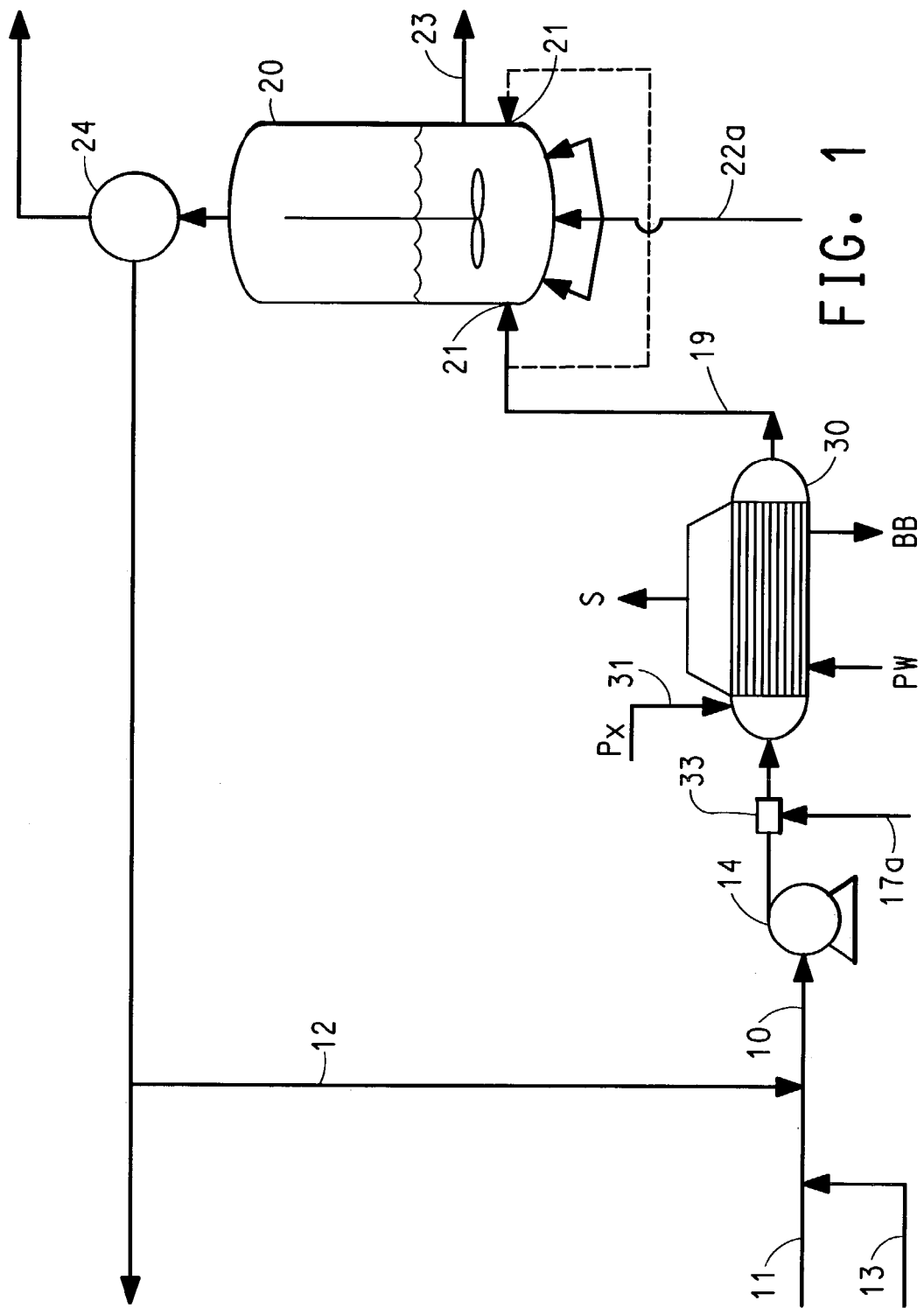
FIG. 1 is a simplified schematic diagram of a preferred embodiment of the invention.

The present invention resides in the discovery that it is possible, when carrying out liquid phase catalytic oxidation of paraxylene in the presence of an acetic acid solvent, to effectively stage the oxidation reaction on a commercial scale into a first high pressure and high solvent ratio reaction zone followed by a second, more conventional, reaction zone and thereby substantially improve process capacity, efficiency and product quality. The present invention is particularly applicable to increasing the capacity of conventional back-mixed oxidation reactors, i.e., "debottlenecking" commercially operating production units, whereby a first reaction zone can be positioned ahead of a second reaction zone which is the conventional reactor, and the resulting output of the staged system can be increased by up to 100% conveniently and without substantial capital investment that would otherwise be required for a new and/or larger and/or redesigned conventional reactor.

According to a preferred embodiment of the invention, the first reaction zone is a plug flow reactor. The term "plug flow reactor" is used herein to define a generally elongated, or tubular, reaction zone in which rapid and thorough radial mixing of the reactants occurs as they flow through the tube or conduit. The invention, however, is intended to embrace any reactor configuration which approximates to a plug flow reaction zone. According to an alternate embodiment of the invention, the first reactor can be a back-mixed reactor, meaning a highly mixed reactor, such as, for example, a stirred tank or a bubble column reactor. For all reactor types which might characterize the first reaction zone according to the invention, the supply of oxygen thereto is essentially pure gaseous oxygen. The first reaction zone is further characterized by a relatively high (compared to conventional paraxylene air-oxidation processes) acetic acid:paraxylene mass ratio in the range of from 5–30:1 and a relatively high (compared to conventional paraxylene air-oxidation processes) pressure, e.g., in the range of from at least 2,500 kpa up to 30,000 kPa or even higher. For the purposes of this disclosure, the solvent:paraxylene mass ratio is defined as follows:

(a) the solvent mass flow is the total solvent flow through the first reaction zone, including any solvent recycled from the second reaction zone and downstream vessels, but excluding solvent recycled within the first reaction zone;

(b) the paraxylene mass flow is the total paraxylene flow to the process, whether the paraxylene is exclusively fed to the first reaction zone or whether a proportion is arranged to bypass the first reaction zone to be fed directly to the second reaction zone.

The operating pressure of the first reaction zone is chosen such that there is no vapor phase present in the first reaction zone, i.e., the first reaction zone is non-boiling. The first reaction zone is optionally cooled to limit the temperature of the reaction medium as it exits the first reaction zone.

The process is carried out in the presence of an oxidation catalyst system, which can be homogeneous or heterogeneous. A homogeneous catalyst is normally used and is selected from one or more heavy metal compounds, such as, for example, cobalt, manganese and/or zirconium compounds. In addition, the catalyst will normally also include an oxidation promoter such as bromine. The catalyst metals and oxidation promoter largely remain in solution throughout the process and are recovered and recycled as a solution, after product recovery, with fresh catalyst make-up.

The feed stream to the first reaction zone contains typical oxidation catalyst components (e.g., Co, Mn, Br), but diluted by a factor of about 3 to 5 relative to the catalyst concentration in recycle mother liquor from product recovery. The catalyst concentration is subsequently raised to more conventional catalyst concentration levels when and as solvent is vaporized and removed overhead in the second reaction zone. The total catalyst metals concentration in the first reaction zone will typically lie in the range 150 to 1,000 ppm w/w, whereas the catalyst metals concentration in the second reaction zone will typically lie in the range of from 500 to 3,000 ppm w/w. When using a Co and Mn metal catalyst system and depending on the water concentration, a total catalyst metals concentration in the first reaction zone of greater than 200 ppm w/w has been observed to give satisfactory activity and selectivity. The oxidation reaction is highly exothermic. Depending on the first reactor solvent ratio and oxygen uptake and without a means of cooling the reaction, the heat of reaction could raise the temperature of the reaction medium to a value in excess of 300° C. A first reactor exit temperature below 300° C. is desirable to minimize acetic acid burn. The first reaction zone may therefore optionally include a cooling coil or other internal or external means for removing heat satisfactorily from the reactor (and reaction medium) to control the exit temperature of the reaction medium below 300° C.

Control of temperature, catalyst concentration, reactor residence time, and maintaining the oxygen supply to the first reaction zone within a predetermined range makes it possible to conveniently limit the uptake of oxygen within the reaction medium to a value which is less than that required for full conversion of the paraxylene present to terephthalic acid.

The invention is characterized in that the terephthalic acid (TA) formed in the first reaction zone remains substantially in solution. By "substantially," the inventors mean that it is preferred to have very little, e.g., less than about 10 percent by weight of solid TA precipitate from solution in the first reaction zone. It is more preferred to have only a trace, e.g., less than 1 percent of solid TA precipitate from solution in the first reaction zone. It is most preferred to avoid precipitation of solid terephthalic acid in the first reaction zone.

Formation of terephthalic acid in the first reaction zone is limited by limiting oxygen uptake in the first reaction zone. Precipitation of terephthalic acid is prevented within the first reaction zone by maintaining a high acetic acid:paraxylene mass ratio, by maintaining a sufficiently high reaction medium temperature, and by selecting an appropriate coolant (e.g., boiling water) and cooling means that avoids cold spots from forming at any location within the reaction zone.

On exiting the first reaction zone, the pressure of the reaction medium is reduced simultaneously as it is fed to the existing conventional back-mixed oxidation reactor. This reactor is typically a stirred tank reactor, but it could also be a bubble column reactor, for example. Pressure reduction can be conveniently accomplished by passing the reaction medium through one or a plurality of pressure letdown valves positioned about the periphery of the reactor. Best results have been obtained when the reaction medium is dispersed rapidly upon entering the second reactor. Rapid dispersion can be achieved by using established methods for dispersing paraxylene-containing feeds in conventional reactors. In a stirred tank reactor, for example, this would include injecting the reaction medium into the reactor below the liquid line in close proximity to the discharge from an agitator impeller. Rapid dispersion of the reaction medium can be achieved in a bubble column reactor by injecting the reaction medium in close proximity to the air feeds.

Referring now to the drawing, FIG. 1 is a simplified schematic diagram of a reactor system according to a preferred embodiment of the invention.

In the illustrated embodiment shown in FIG. 1, the invention is carried out by first positioning a first reactor 30 upstream of conventional reactor 20 (i.e., second reactor), and forming a feed stream 10 comprising acetic acid, water and oxidation catalyst for feeding first reactor 30. In practice the feed stream will comprise a mixture of (i) recycled acetic acid, recycled mother liquor and catalyst, line 11, (ii) reactor condensate from the second reactor, line 12, and (iii) fresh acetic acid make-up, line 13. The mixed feed stream will contain typical catalyst components (e.g., Co, Mn, Br), but diluted compared to their respective concentrations in the second reaction zone, that is, the conventional oxidation reactor. Optionally, although not shown, catalyst concentration can be controlled in the first reaction zone by feeding a portion of the catalyst-containing mother liquor, line 11, recycled from another part of the process, directly into second reactor 20.

The mixed feed stream 10 will generally have a temperature in the range of from 130° C. to 160° C., based on the temperature of the various components which form the feed stream. A temperature in the range of from 130° C. to 160° C. has been found to be satisfactory for initiating the oxidation reaction.

In the illustrated embodiment, the pressure of mixed feed 10 is raised to a value in the range of at least, but generally in excess of about, 2,500 kPa by any suitable pumping means 14. The pressure is chosen to ensure that all of the gaseous oxygen, introduced via line 17a, will be readily dissolved in the feed stream ahead of first reactor 30 as shown. The mixed feed stream with dissolved oxygen is then fed simultaneously and continuously into plug flow reactor 30 with paraxylene being fed via line 31, and the reaction is initiated. The paraxylene may optionally be pre-mixed with acetic acid solvent and the mixture fed via line 31.

While it is generally preferable to feed all the paraxylene to the first reactor 30, the option of bypassing a portion of the feed paraxylene directly to the second reactor 20 is included within the scope of the invention. In cases where a portion of paraxylene feed 31 is fed directly to second reactor 20, the resulting solvent:paraxylene mass ratio in the reaction medium in the first reactor will adjust upwardly in response to that portion of the paraxylene feed which bypasses the first reactor, and the resulting mass ratio may, therefore, reach a value in the range of from 80:1 up to values in the range of 100:1 and even higher.

Molecular oxygen is dissolved in the mixed feed stream using any convenient in-line mixing device 33 to achieve a concentration of dissolved oxygen in the mixed feed stream of up to 5.0% w/w. Mixing device 33 could be an in-line nozzle arranged to discharge oxygen directly into the feed stream. In-line static mixers (not shown) can also be positioned upstream of first reactor 30 to facilitate mixing.

It is also possible according to the invention to stage the introduction of oxygen, i.e., to introduce the oxygen at a plurality of locations along the length of first reaction zone 30. By staging oxygen injection, the maximum local dissolved oxygen concentration is reduced, which, in turn, allows reactor operating pressure to be reduced. Reducing reactor operating pressure reduces the cost of the reactor, feed pump, oxygen compressor and associated equipment.

Residence time of the reaction medium within plug flow reaction zone 30 is relatively short, i.e., less than 6 minutes.

The reactor 30 shown in FIG. 1 is a shell and tube design. The reaction medium flows through the tubes, while a coolant, e.g., pressurized water (PW), is introduced into the shell side where it boils and is removed as steam (S). A small water purge (boiler blowdown, BB) is taken to control impurity/residue build-up in the water system.

The temperature of the reaction medium as it exits first reactor 30 is controlled by controlling the pressure of the produced steam, and hence its temperature. Controlling the process parameters as described according to the invention makes it possible to limit the uptake of oxygen within the reaction medium in the first reaction zone to a value which is less than 70% of the oxygen required for full conversion of the paraxylene to TA. Thus, paraxylene is converted in first reactor 30 primarily to TA intermediates, such as p-tolualdehyde, p-toluic acid and 4-CBA. Under the described process conditions the first reactor will not produce any solid TA.

Figure 2:
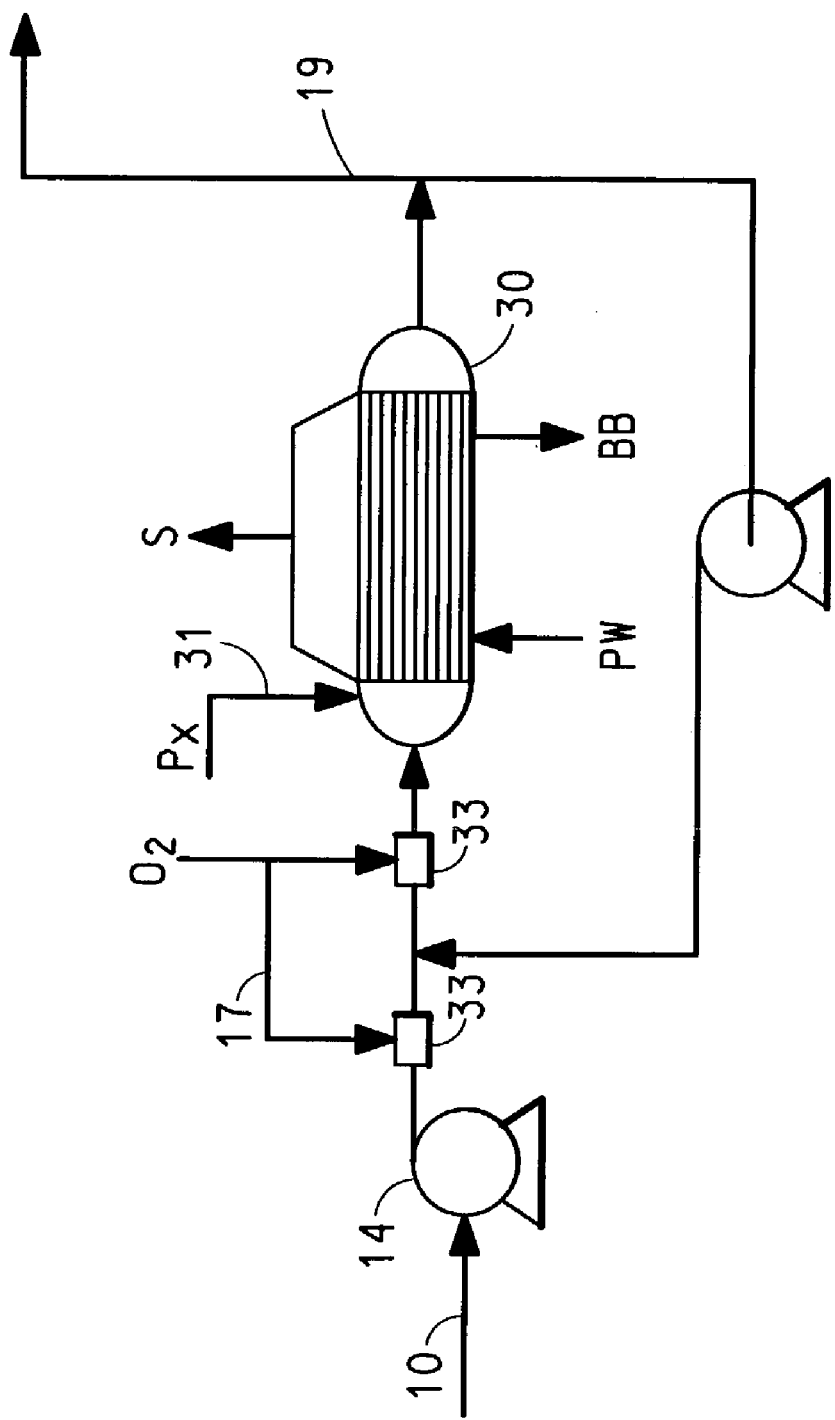
FIG. 2 is a simplified schematic diagram of an alternative to the process diagram shown in FIG. 1 wherein a pumped circulating loop reactor with recycle is illustrated.

Although a shell and tube reactor design is shown in FIG. 1, reactor can be any suitable reactor design with provisions for optional heat removal and optional multiple oxygen injection. For example, the reactor can have multiple tube passes, with optional oxygen injection into the reaction medium upstream of each tube pass. Alternatively, the reactor can be a single cooled or uncooled (adiabatic) stirred tank reactor with oxygen injection upstream of and/or into the reactor. Alternatively, the reactor can be a series of cooled or uncooloed stirred tank reactors with oxygen injection upstream of and/or into each reactor. As a further alternative, a back-mixed reactor can be employed, such as, for example, a pumped circulating loop reactor, with oxygen injection into the loop and optional heat removal from the loop as illustrated in FIG. 2.

The reaction medium exiting plug-flow first reactor 30 is fed via line 19 to a second reactor, i.e., oxidation zone, 20, which, as shown, is the conventional, continuously stirred tank reactor of the existing process which is the subject of debottlenecking. Simultaneously, the pressure of the reaction medium is reduced to a value in the range of from about 500 kPa to less than 2,500 kPa. Pressure reduction can be conveniently accomplished by passing the reaction medium through one or a plurality of pressure letdown valves or nozzles 21 positioned about the periphery of reactor 20 whereby the reaction medium is dispersed rapidly by injection into an agitator impeller region below the liquid line of the reactor. Most process conditions within reactor 20, i.e., temperature, pressure and catalyst concentration are within conventional ranges, although residence time is reduced. A fresh supply of air or oxygen-containing gas, line 22a, is introduced and rapidly dispersed into the reaction medium in second reactor 20 by any convenient means.

TA will precipitate to form a slurry within the second, conventional, reactor 20, and it can be recovered from the reactor system via line 23 using conventional methods. Overhead vapor from reactor 20, which will necessarily contain some acetic acid and water, is condensed via condenser 24, and most of the condensate is returned, i.e., recycled, via line 12 for feed stream make-up to first reactor 30. A proportion of the acetic acid and water condensate stream (so-called water draw off) is diverted to a solvent dehydration system to remove the water of reaction. Optionally, but not shown, a portion of the condensate may be returned to reactor 20, to the reactor headspace, via a reflux slinger, and/or to the reaction zone, via a separate feed line or by mixing with the existing feed stream, line 19. Optionally, but not shown, the overhead vapor from reactor 20 may be fed to a rectifier column, with the bottom product, or condensate, from the rectifier recycled, via line 12, for feed stream make-up to first reactor 30.

The invention provides an economical and reliable method for staging the TA oxidation reaction whereby the production capacity of a conventional single-stage oxidation reactor of the type found in many commercially operating terephthalic acid processes can be increased by up to 100%.

What is claimed is:

1. A process for increasing the production capacity of a conventional back-mixed oxidation reactor for catalytic liquid phase, air oxidation of paraxylene to terephthalic acid, said method comprising:
   (a) positioning a first reaction zone upstream of a second zone comprising said conventional back-mixed oxidation reactor;
   (b) feeding acetic acid, oxidation catalyst, paraxylene, and a supply of oxygen to said first reaction zone to form a reaction medium in which the acetic acid:paraxylene mass ratio is in the range of from 13–16:1 and the operating pressure is at least about 2,500 kPa;
   (c) limiting the uptake of oxygen within the reaction medium in said first reaction zone to a value which is less than that required for full conversion of the paraxylene present to terephthalic acid, wherein said terephthalic acid produced in the reacton medium in the first reaction zone remains in solution; and then
   (d) feeding the reaction medium to said conventional back-mixed oxidation reactor in said second reaction zone while simultaneously reducing the pressure of the reaction medium to a value in the range of from about 500 kPa to less than 2,500 kPa;
   (e) vaporizing a portion of the acetic acid present in said conventional back end reactor in said second zone;
   (f) removing the vapor from the reactor overhead;
   (g) condensing the vapor; and
   (h) recycling some or all of the condensate to the first reaction zone.

2. The process of claim 1 in which said first reaction zone is a plug flow reactor or a back-mixed reactor.

3. The process of claim 2, wherein less than 10 percent by weight of the terphthalic acid precipitates as a solid in the first reaction zone.

4. The process of claim 3, wherein less than 1 percent by weight of the terephthalic acid precipitates as a solid in the first reaction zone.

5. The process of claim 4, wherein there is no precipitation of the terephthalic acid as a solid in the first reaction zone.

6. The process of claim 1, wherein the oxygen uptake within the reaction medium in said first reaction zone is limited to a value less than 70 percent of that required for full conversion of the paraxylene to the terephthalic acid.

7. The process of claim 6, wherein the oxygen uptake within the reaction medium in said first reaction zone is limited to a value in the range of from 40 to 60 percent of that required for full conversion of the paraxylene to the terephthalic acid.

8. The process of claim 1 which includes the additional step of diverting a portion of the paraxylene feed from the first reaction zone directly to the convention back-mixed oxidation reactor whereby the resulting acetic acid:paraxylene mass ratio in the reaction medium in the first reaction zone is adjusted upwardly in response to that portion of the paraxylene feed which bypasses the first reaction zone to achieve a corresponding value in excess of 13:1.

9. The process of claim 2 which includes the additional step of diverting a portion of the paraxylene feed from the first reaction zone directly to the conventional back-mixed oxidation reactor whereby the resulting solvent:paraxylene mass ratio in the reaction medium in the first reaction zone is adjusted upwardly in response to that portion of the paraxylene feed which bypasses the first reaction zone to achieve a corresponding value in excess of 25:1.

10. A process for increasing the production capacity of a conventional back-mixed oxidation reactor for catalytic liquid phase, air oxidation of paraxylene to terephthalic acid, said method comprising:
   (a) positioning a first reaction zone upstream of said conventional back-mixed oxidation reactor;
   (b) forming a feed stream comprising acetic acid and oxidation catalyst at a pressure of at least 2,500 kPa;
   (c) oxygenating the feed stream;
   (d) continuously and simultaneously feeding (1) the oxygenated feed stream and (2) paraxylene to said first reaction zone to form a reaction medium in which the acetic acid:paraxylene mass ratio is in the range of from 13–16:1;
   (e) limiting the uptake of oxygen within the reaction medium in said first reaction zone to a value which is less than that required for full conversion of the paraxylene present to terephthalic acid, wherein said terephthalic acid produced in the reaction medium in the first reaction zone remains in solution;

(f) feeding the reaction medium to a said conventional back-mixed oxidation reactor in said second reaction zone while simultaneously reducing the pressure of the reaction medium to a value in the range of from about 500 to less than 2,500 kPa;

(e) vaporizing a portion of the acetic acid present in said conventional oxidation reactor in said second reaction zone;

(f) removing the vapor from the reactor overhead;

(g) condensing the vapor; and (h) recycling some or all of the condensate to the feed stream.

11. The process of claim 10, wherein less than 10 percent by weight of the terephthalic acid precipitates as a solid in the first reaction zone.

12. The process of claim 11, wherein less than 1 percent by weight of the terephthalic acid precipitates as a solid in the first reaction zone.

13. The process of claim 12, wherein there is no precipitation of the terephthalic acid as a solid in the first reaction zone.

14. The process of claim 10, wherein the oxygen uptake within the reaction medium in said first reaction zone is limited to a value less than 70 percent of that required for full conversion of the paraxylene to the terephthalic acid.

15. The process of claim 14, wherein the oxygen uptake within the reaction medium in said first reaction zone is limited to a value in the range of from 40 to 60 percent of that required for full conversion of the paraxylene to the terephthalic acid.

16. The process of claim 10 which includes the additional step of diverting a portion of the paraxylene feed from the first reaction zone to said conventional reactor whereby the resulting acetic acid:paraxylene mass ratio in the reaction medium in the first reaction zone is adjusted upwardly in response to that portion of the paraxylene feed which bypasses the first reaction zone to achieve a corresponding value in excess of 13:1.

* * * * *